US00PP28790P3

(12) United States Plant Patent
Ballington et al.

(10) Patent No.: US PP28,790 P3
(45) Date of Patent: Dec. 26, 2017

(54) BLUEBERRY PLANT NAMED 'HEINTOOGA'

(50) Latin Name: ***Vaccinium*×[*V. formosum* (syn. *V. australe, V. corymbosum*)×(*V. constablaeii*×*V. virgatum*)]**
Varietal Denomination: Heintooga

(71) Applicant: North Carolina State University, Raleigh, NC (US)

(72) Inventors: James R. Ballington, Cary, NC (US); William T. Bland, Castle Hayne, NC (US)

(73) Assignee: North Carolina State University, Raleigh, NC (US)

( * ) Notice: Subject to any disclaimer, the term of this patent is extended or adjusted under 35 U.S.C. 154(b) by 43 days.

(21) Appl. No.: 14/998,766

(22) Filed: Feb. 12, 2016

(65) Prior Publication Data

US 2017/0188494 P1 Jun. 29, 2017

Related U.S. Application Data

(60) Provisional application No. 62/387,278, filed on Dec. 23, 2015.

(51) Int. Cl.
*A01H 5/08* (2006.01)

(52) U.S. Cl.
USPC ..... Plt./157

(58) Field of Classification Search
USPC ..... Plt./157
CPC ..... A01H 5/08; A01H 5/00
See application file for complete search history.

(56) References Cited

PUBLICATIONS

North Carolina State Univ submitted to CRIS *Vaccinium* Breeding and Genetics Project End Date Sep. 30, 2010, 16 pp.*
10th International Symposium on *Vaccinium* and Other Superfruits. Jun. 17-22, 2012. Maastricht, Netherlands. Abstract entitled *NC 2701, a promising trispecies pentaploid blueberry selection from North Carolina.* James Ballington and Terry Bland. pp. 2.
Ballington J.R. *Blueberry cultivars released from North Carolina State University blueberry breeding program.* Jun. 30, 2015, pp. 3.
Current status of the NCSU Breeding Program; published in 2013; pp. 1.
North Carolina State University submission to the USDA Current Research Information System (CRIS) entitled: *Vaccinium Breeding and Genetics.* Project No. NC03647. Project start date: Oct. 1, 2005; Project end date: Sep. 30, 2010, (pp. 2, 4, and 5 discuss the new variety NC 2701 that is being developed) pp. 16.
North Carolina State University submission to the USDA Current Research Information System (CRIS) entitled: *Blueberry and Muscadine Grape Breeding.* Project No. NC02366. Project start date: Oct. 1, 2010; Project end date: Sep. 30, 2015, pp. 5.
Progress with the Blueberry Breeding Program at North Carolina State University, published in 2011; (variety NC 2701 discussed on pp. 37-39 and 43-44) pp. 8.

* cited by examiner

*Primary Examiner* — June Hwu
(74) *Attorney, Agent, or Firm* — Myers Bigel, P.A.

(57) ABSTRACT

'Heintooga' is a new and distinct variety of blueberry plant that has the following unique combination of desirable features outstanding in a new variety. Heinetooga has slightly less than one fully developed seed per berry so that the fruit should be perceived as seedless by most consumers. Heinetooga has a medium to large fruit size with very good fruit color, picking scar and flavor. The fruit firmness of Heinetooga is moderately good to good and post harvest shelf-life is good so the fruit is suitable for shipping. Further, Heinetooga has broad soil adaptation.

3 Drawing Sheets

STATEMENT REGARDING ELECTRONIC FILING OF A SEQUENCE LISTING

A Sequence Listing in ASCII text format, submitted under 37 C.F.R. §1.821, entitled 5051-895_ST25.txt, 1,862 bytes in size, generated on Oct. 11, 2017 and filed via EFS-Web, is provided in lieu of a paper copy. This Sequence Listing is hereby incorporated by reference herein into the specification for its disclosures.

Latin name of the genus and species: The Latin name of the novel blueberry trispecies hybrid variety disclosed herein is *Vaccinium*×[*V. formosum* (syn. *V. australe, V. corymbosum*) (see Weakley, 2012)×(*V. constablaeii*×*V. virgatum*)].

Variety denomination: The inventive trispecies hybrid *Vaccinium* cultivar designated as *Vaccinium*×[*V. formosum*×(*V. constablaeii*×*V. virgatum*)] disclosed herein has been given the variety denomination 'Heintooga'.

BACKGROUND OF THE INVENTION

The present invention relates to a new and distinct trispecies hybrid cultivar designated as *Vaccinium*×[*V. formosum*×(*V. constablaeii*×*V. virgatum*)] (blueberry) grown as a fruiting woody shrub for commercial agriculture. Blueberries are typically consumed both fresh and in a number of processed products.

This new and distinct variety of blueberry plant originated from the hand pollinated cross of 'Bluechip' (*V. formosum*) (unpatented) (2n=4X=48 chromosomes)×NC 1827 [PI346603 (*V. constablaeii*)×'Premier' (*V. virgatum*)] (unpatented) (2n=6X=72 chromosomes) made in a greenhouse in Raleigh, N.C., by James R. Ballington in 1978. The progeny that resulted from this cross is pentaploid with 2n=5X=60 chromosomes. Seedlings were established in 1979 at the Horticultural Crops Research Station at Castle Hayne, N.C., and a single "fully fruitful" seedling, designated as experimental selection NC 2701, was selected by James R. Ballington in 1984. Of the progeny, NC 2701 was the single seedling with a full crop of fruit. In addition, it was selected for medium to large fruit size, desirable fruit color, picking scar, firmness, flavor and low numbers of seeds per berry. As is typical with pentaploids, NC 2701 produces very little viable pollen and requires cross-pollination for fruit set and development.

NC 2701 was first established in observation trials at Jackson Springs, N.C., and based on its performance in these trials was repropagated by stem cuttings and established in replicated trials in Castle Hayne, N.C. and Jackson Springs, N.C. NC 2701 was also established in an observation trial on one commercial blueberry farm in Ivanhoe, N.C., under a Memorandum of Agreement with North Carolina State University. In addition, in 2014, NC 2701 was established in observation trials through Material Transfer Agreements between North Carolina State University, the USDA blueberry breeding program at Corvallis, Oreg., and the Rutgers University blueberry breeding program at Chatsworth, N.J. With these three agreements the University retains ownership of the plants and the grower or breeding program provides the land and care of the plants. This new variety has been named the 'Heintooga' cultivar, due to the similarity of its fruit quality to its wild *V. constablaeii* grandparent, PI 346603, which was collected on Heintooga Ridge Spur Road in western North Carolina in 1967.

SUMMARY OF THE INVENTION

'Heintooga' is a pentaploid trispecies hybrid blueberry variety. As is typical for pentaploids it produces little or no viable pollen and requires cross-pollination for fruit set and development. Rabbiteye blueberry varieties such as 'Ira', 'Onslow' and 'Powderblue' (all unpatented) are recommended for cross-pollination of 'Heintooga' in the southern US, and the hexaploid hybrid 'Little Giant' (unpatented), or highbush varieties, in northern regions. The fruit averages just under one fully developed seed per berry and should be perceived as seedless by most consumers. 'Robeson' pentaploid (U.S. Plant Pat. No. 19,756) produces only 3 fully developed seeds per berry, but this is still three times as many as 'Heintooga'. Plant size is smaller and less vigorous than rabbiteye blueberry varieties such as 'Premier' (unpatented) or the vigorous pentaploid variety 'Robeson', so yield potential per plant is lower. However this can be compensated for by spacing 'Heintooga' plants closer together in the row resulting in higher numbers of plants per acre. 'Heintooga' differed consistently from 'Robeson' for dormant and first flush stem color, leaf dimensions, leaf margins, flower dimensions, fruit color with bloom and seed shape. 'Heintooga' ripens with late midseason to late ripening northern and southern highbush varieties. Fruit size is medium to large. Berry color, picking scar and flavor are consistently in the very good range. Flavor is sweet and highly aromatic, similar to the *Vaccinium constablaeii* grandparent of 'Heintooga'. Berry firmness of 'Heintooga' is moderately good to good, significantly better than 'Premier' or 'Robeson', and adequate for long distance shipping. Post harvest shelf-life is good following seven days storage at 4.5° C. Plants of 'Heintooga' are broadly adapted to soils. 'Heintooga' has a semi-upright plant habit in contrast to 'Robeson' which has an upright growth habit. Plants of 'Heintooga' have remained true to type through successive cycles of asexual propagation. Dormant buds on 'Heintooga' plants have an estimated chilling requirement between 800 and 1000 hours below 4.5° C. 'Heintooga' was first propagated by leafy cuttings in August 1984 in Raleigh, N.C.

BRIEF DESCRIPTION OF THE DRAWINGS

This new blueberry plant is illustrated by the accompanying photographs provided in FIG. 1 and FIG. 2, which show the plant's form, foliage and fruit. The photographs in the drawings were made using digital photography techniques and illustrate colors as true as can be reasonably obtained when using these techniques. Colors in the photographs may differ slightly from the color values cited in the detailed botanical description, which accurately describe the colors of the new *Vaccinium* variety.

FIG. 3 shows a hypothetical example of one SSR marker on a panel of 6 cultivars depicted as 1-6. The lane marked as M shows the standard marker lane with known fragment size in base pair (bp). The top arrow shows a monomorphic band that is identical in all cultivars. The bottom arrow shows a band that is monomorphic in cultivar 3, 4 and 6. Therefore the other band can be used to distinguish these three cultivars from each other. This profile for these cultivars is based on one markers. As the number of markers increase the probability that two literally different cultivars have the same profile will reduced.

DETAILED BOTANICAL DESCRIPTION

Figure 1:
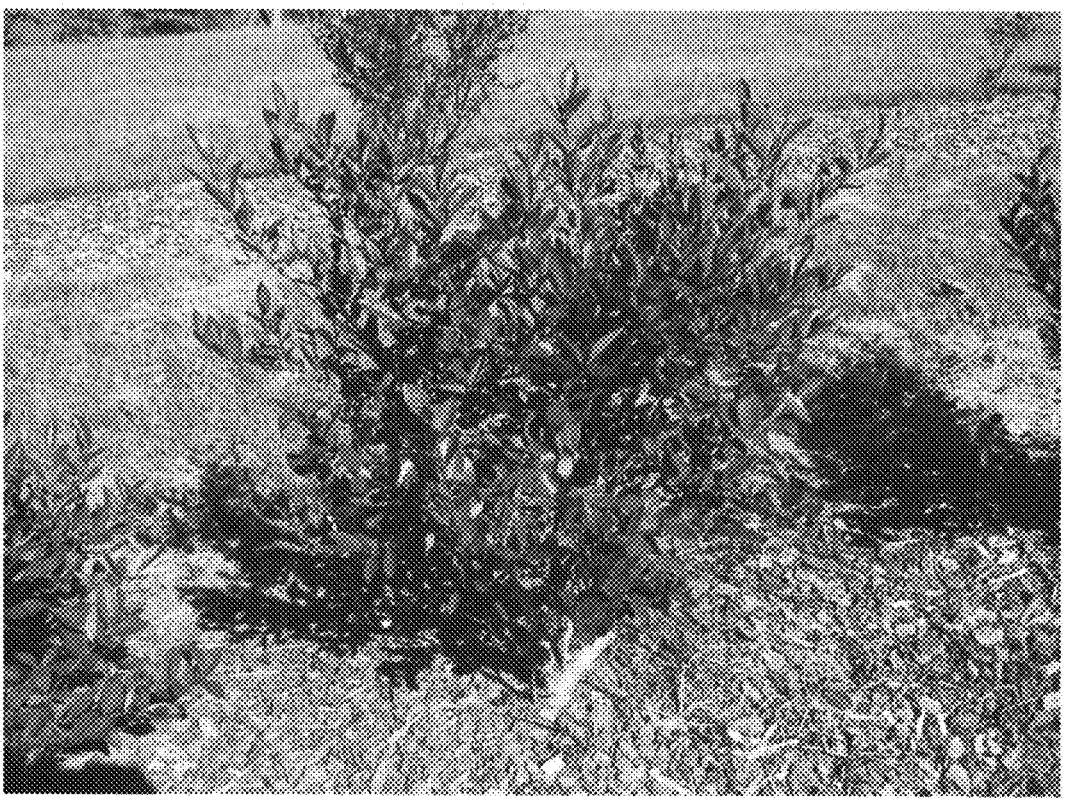
FIG. 1 illustrates the typical plant habit of 'Heintooga' and was taken from a five-year old plant growing at the North Carolina. Agricultural Research Service Station at Jackson Springs, N.C.

The following is a detailed botanical description of a new and distinct variety of pentaploid trispecies *Vaccinium* hybrid known as 'Heintooga'. The observations below are from mature plants grown in a replicated trial at standard commercial plant spacing for rabbiteye blueberry varieties of 1.9 m between plants in rows and 3.9 m between rows, at Castle Hayne, N.C., with four replications of four plants per replication. Those skilled in the art of cultivar description and evaluation will appreciate that certain characteristics of a variety will vary with older, or conversely, younger plants. 'Heintooga' has not been observed under all possible environmental conditions. Where dimensions, sizes, colors and other characteristics are given, it is to be understood that such characterizations are approximations or averages set forth as accurately as practicable. The phenotype of the variety may differ from the description herein with variations in the environment such as season, temperature, light intensity, day length and cultural conditions. Color notations are based on The Royal Horticultural Society Colour Chart, The Royal Horticultural Society, London, UK, 4th edition, 2001.

For botanical description purposes 'Heintooga' was compared to 'Robeson' (U.S. Plant Pat. No. 19,756) (Ballington and Rooks, 2009), another recent pentaploid hybrid release from North Carolina State University. It was not feasible to compare 'Heintooga' with its female parent 'Bluechip' because the latter is extremely susceptible to the stern blight fungus (*Botryosphaeria dothidea*) to the point that it is impractical to establish and maintain for comparison purposes. Only two plants remain of the male parent, NC 1827, and they are established at the Sandhills Research Station, at Jackson Springs, rather than at Castle Hayne. So, with the exception of characters that would not vary across locations, it was not feasible to compare 'Heintooga' to NC 1827 either. In this regard, 'Heintooga' does differ from NC 1827 for plant habit, semiupright for 'Heintooga' versus spreading for NC 1827, and leaf margins, entire for 'Heintooga' versus serrulate for NC 1827. The botanical descriptive data presented below are averages of data collected from 2009-2013 from mature plants (seven to eleven years old) grown in Castle Hayne, N.C.

Technical Description of the Variety and Comparison to Blueberry Variety 'Robeson'

Plant:

*Dimensions*.—Heintooga — 1.5 m height, 1,5 m width, H/W ratio 1. Robeson — 2.4 m height, 1.8 m width, H/W ratio 1.33.

*Mature stem diameter*.—Heintooga — 1.5 to 3 cm. Robeson — 2.5 to 5 cm.

*Mature stem length*.—Heintooga — 108 cm. Robeson — 135 cm.

*Number of mature stems per bush*.—Heintooga — 8 to 10. Robeson — 4 to 6.

*Number of renewal stems*.—Heintooga — 2.7. Robeson — 2.8.

*Internode length on first flush growth*.—Heintooga — 11 cm. Robeson — 13 cm.

*Dormant mature stem color*.—Heintooga — brown (RHS N200D). Robeson — brown (RHS 200C).

*Dormant one year stem color*.—Heintooga — greyed-purple (RHS 183B) on exposed surface; greyed-orange (RHS 175B) on unexposed surface. Robeson — greyed-orange (RHS 174B) on exposed surface; yellow-green (RHS 148B) on unexposed surface.

*First flush growth stem color in summer*.—Heintooga — greyed-orange (RHS 175B) on exposed surface; green (RHS 138C) on unexposed surface. Robeson — green (RHS 138C) on exposed and unexposed surfaces.

*Pubesence on summer and one year dormant stems*.—None either Heintooga or Robeson.

Leaves:

*Leaf blade dimensions*.—Heintooga — 55 mm length (L), 25 mm width (W), L/W ratio 2.2. Robeson — 62 mm length, 32 mm width, L/W ratio 1.9.

*Leaf petiole length*.—Heintooga — 3 mm. Robeson — 4 mm.

*Leaf shape*.—Heintooga — narrowly elliptic. Robeson — mostly acuminate to occasionally acute.

*Leaf apex angle*.—Heintooga — acuminate. Robeson — mostly acuminate to occasionally acute.

*Leaf base angle*.—Acute for both Heintooga and Robeson.

*Leaf margin*.—Heintooga — entire. Robeson — sparsely serrulate on apical one third.

*Leaf pubescence*.—None for either Heintooga or Robeson.

*Leaf glands*.—None on either surface for Heintooga or Robeson.

*Leaf color*.—Heintooga — green (RHS 136A 137A) on the adaxial surface; green (RHS 138A-139A) on the abaxial surface. Robeson — green (RHS 136B-137B) on the adaxial surface; green (RHS 138A-N138B) on the abaxial surface.

*Vegetative bud burst*.—Heintooga — mid-season. Robeson — early.

Flowers:

*Number of flower petals*.—Five for Heintooga and Robeson, fused completely along the margins into a corolla tube so that they cannot be separated for individual measurements.

*Number of flowers per inflorescence*.—Heintooga — 8 to 9. Robeson — 7 to 8.

*Flower dimensions*.—Heintooga — 8 mm length, 5.5 mm width, L/W ratio 1.45. Robeson — 7 mm length, 7 mm width, L/W ratio 1.

*Length of the single style*.—Heintooga and Robeson 8 mm for both.

*Length of stamens*.—Heintooga — 7 mm. Robeson — 6 mm.

*Flower shape*.—Heintooga — urceolate to cylindro-urceolate. Robeson — urceolate.

*Color of petals on fully opened flowers*.—White (RHS 155C) for both Heintooga and Robeson with red-purple (RHS N66B-N66D) on exposed corolla lobes.

*Corolla*.—Ridges are present on the corolla of Heintooga and Robeson, and indicated by red-purple Color (RHS N66B-N66D) verses white (RHS 155C) for the remainder of the corolla.

*Bud bloom burst*.—Moderate for Heintooga.

Figure 2:
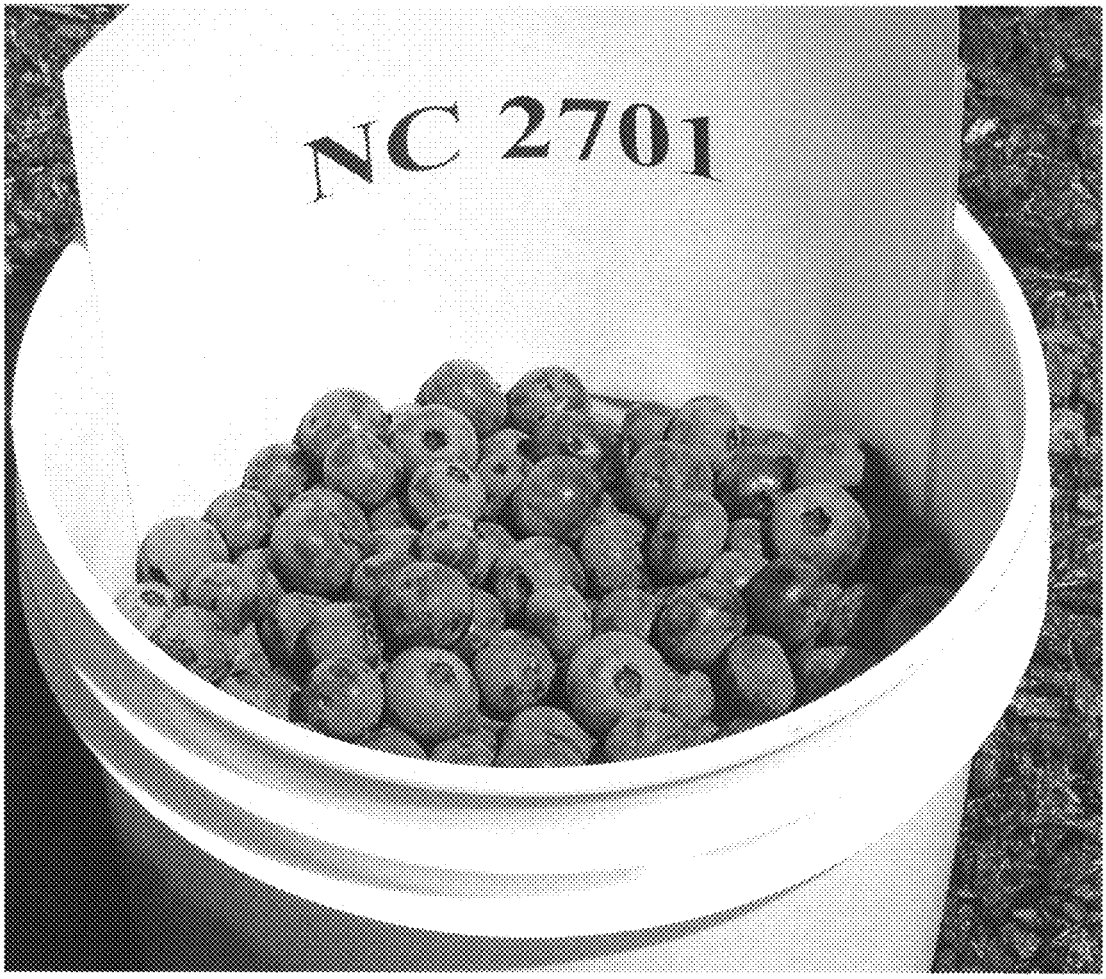
FIG. 2 illustrates the typical fruit of 'Heintooga' growing at the Horticultural Crops Research Station at Castle Hayne, N.C. The fruit was harvested from four-year old plants.

Fruit: (See, FIG. 2).

*Fruit dimensions*.—Heintooga — 12 mm length, 14 mm width, L/W ratio 0.86. Robeson — 13 mm length. 14 mm width, L/W ratio 0.9.

*Fruit shape*.—Heintooga — round to mostly oblate. Robeson — round to oblate.

*Fruit cluster density*.—Medium for Heintooga and Robeson.

*Fruit pedicel length*.—Heintooga — 7 mm. Robeson — 8 mm.

*Fruit pedicel color*.—Yellow-green (RHS 148B) for Heintooga and Robeson.

*Fruit nicking scar diameter*.—Heintooga — 1-2 mm. Robeson — 2 mm.

*Fruit calyx orientation*.—Heintooga — mostly appressed against the apical end of the berry. Robeson — appressed.

*Fruit calyx prominence*.—Not prominent on Heintooga or Robeson.

*Fruit calyx diameter*.—5-7 mm for Heintooga. New Hanover and O'Neal.

*Depth of calyx basin*.—Shallow to medium for Heintooga and Robeson.

*Fruit color with bloom (epicuticular wax)*.—Heintooga — violet-blue (RHS 97C). Robeson — blue (RHS 100C).

*Fruit color without bloom*.—Black (RHS 202A) for both Heintooga and Robeson.

*Fruit acidity*.—Heintooga — low. Robeson — moderate.

*Fruiting type*.—Fruiting only occurs on one year old shoots for Heintooga and Robeson.

*Fruit sweetness*.—Medium for Heintooga.

Fruit sepals:

*Fruit sepal number*.—Five for Heintooga and Robeson.

*Fruit sepal shape*.—Ovate for Heintooga and Robeson.

*Fruit sepal length*.—Heintooga — 1.4 mm. Robeson — 1.2 mm.

*Fruit sepal width*.—Heintooga — 2.2 mm. Robeson — 2.0 mm.

*Fruit sepal apex*.—Heintooga — acute to occasionally acuminate. Robeson — acute.

*Fruit sepal base*.—Acute and fused to the fruit skin for Heintooga and Robeson.

*Fruit sepal margin*.—Entire for Heintooga and Robeson.

*Fruit sepal outer surface color*.—Heintooga — Violet-blue (RHS 97C). Robeson — Blue (RHS 100C).

*Fruit sepal inner surface color*.—Black (RHS 202A) for Heintooga and Robeson.

*Fruit sepal attitude*.—Appressed (flattened) for Heintooga and Robeson.

Seeds:

*Number of fully developed seeds per berry*.—Heintooga — 0.9 average (range 0.0-2.0). Robeson — 3.1 average (range 2.5-3.65).

*Seed dimensions*.—Heintooga — 1.75 mm length. 1.0 mm width, L/W ratio 1.75. Robeson — 1.5 mm length, 1.0 mm width, L/W ratio 1.5.

*Seed shape*.—Heintooga — depressed shallowly arcuate. Robeson — depressed ovate.

Distinctive Characteristics of 'Heintooga' Based on Botanical Data

'Heintooga' differs consistently from 'Robeson' for plant vigor as determined by plant dimensions, 1.5 m height by 1.5 m width for 'Heintooga' versus 2.4 m height by 1.8 m width for 'Robeson'; mature stem length, 108 cm for 'Heintooga' versus 135 cm for 'Robeson'; number of mature stems, 8-10 for 'Heintooga' versus 4-6 for 'Robeson'; and average annual length of new stems, 36 cm for 'Heintooga' versus 46 cm for 'Robeson'. They also consistently differ for dormant one year stem color, greyed-purple (RHS 183B) on the exposed surface and greyed-orange (RHS 175B) on the unexposed surface for 'Heintooga' versus greyed-orange (RHS 174B) on the exposed surface and yellow-green (RHS 148B) on the unexposed surface for 'Robeson'; first flush stem color in summer, greyed-orange (RHS 175B) on the exposed surface for 'Heintooga' versus green (RHS 138C) on the exposed surface for 'Robeson'; leaf blade dimensions, 55 mm length by 25 mm width for 'Heintooga' versus 62 mm length by 32 mm width for 'Robeson'; leaf margin, entire for 'Heintooga' and sparsely serrulate on the apical one third for 'Robeson'; flower dimensions, 8.0 mm length by 5.5 mm width for 'Heintooga' versus 7.0 mm length by 7.0 mm width for 'Robeson'; fruit color with bloom, violet-blue (RHS 97C) for 'Heintooga' versus blue (RHS 100C) for 'Robeson'; number of fully developed seeds per berry, 0.9 average for 'Heintooga' versus 3.1 average for 'Robeson'; and seed shape, depressed shallowly arcuate for 'Heintooga' versus depressed ovate for 'Robeson'.

For technical (pomological) description purposes 'Heintooga' was compared to 'Robeson' and 'Premier' (unpatented) in the replicated trial at Castle Hayne, N.C., in 2005-2007. This trial is described in the previous section. 'Premier' was included in the trial to serve as a pollinator variety for the two pentaploid varieties, 'Heintooga' and 'Robeson'. Data for time of bloom was however collected from Jackson Springs, N.C., in 2014 because it was considered to be more representative.

Time of Flowering

Table 1 presents representative bloom data comparing 'Heintooga' to 'Robeson' and 'Premier' at Jackson Springs, N.C., in 2014. Date of first bloom for 'Heintooga' was three days later than 'Robeson' and four days later than 'Premier'. 'Heintooga' was one day later than 'Robeson' and four days earlier than 'Premier' for date of 50 percent bloom. 'Heintooga' was four days later than 'Robeson' for date of last bloom. It was not feasible to determine the date of last bloom for 'Premier' because it is a very large plant and the majority of the flowers are abnormal with only a partially developed corolla or no corolla at all (Sampson, et al., 2014).

TABLE 1

Time of flowering of blueberry cultivars, 'Heintooga', 'Robeson' and 'Premier', Jackson Springs, NC. 2014[1]

| | Bloom dates | | |
|---|---|---|---|
| Cultivar | First bloom | 50% bloom | Last bloom |
| Heintooga | 3/26 | 4/8 | 4/18 |
| Robeson | 3/23 | 4/7 | 4/22 |
| Premier | 3/22 | 4/12 | NA[2] |

[1]Estimated from field observations.

[2]Not available as it was not feasible to determine date of last bloom on 'Premier' due to the size of the plant and abnormal corolla development.

Pollen Production and Pollination Requirements

The flowers of 'Heintooga' produce little or no viable pollen so they require cross pollination for fruit set and development. The rabbiteye blueberry (*V. virgatum*) cultivars 'Ira', 'Onslow' and 'Powderblue' (all unpatented) are recommended as pollinator varieties in the southern US. 'Premier' also overlaps in bloom with 'Heintooga' (Table 1) and was the pollinator in the replicated trial at Castle Hayne, N.C., however it tends to bloom early in some years and its abnormal flower morphology makes 'Premier' especially subject to frost and freeze injury, so it is no longer recommended as a pollinator for 'Heintooga'. The hexaploid interspecific hybrid cultivar 'Little Giant' (unpatented) (USDA, ARS. Release notice for 'Little Giant', 1995) or northern highbush varieties are recommended as pollinators for 'Heintooga' in colder regions because rabbiteye blueberry cultivars are not hardy outside the southern US.

Ripening Season

Season of ripening is represented by percent ripe fruit by mid-Jure (Table 2). On average, 'Heintooga' had 32 percent more ripe fruit by mid June than 'Robeson' and 52 percent more than 'Premier'. In 2007, ripening data was available for comparison with the southern highbush cultivar 'Legacy' (*V. formosum*) (unpatented, USDA, 'Legacy' release notice, 2001) and the percent ripe fruit for this cultivar and 'Heintooga' was very similar. 'Legacy' is considered late midseason to late season ripening. 'Heintooga' appears to ripen with late midseason to late season highbush and southern highbush type blueberries as opposed to between highbush and rabbiteye, which is typical for pentaploids in *Vaccinium* (Galletta and Ballington, 1996).

TABLE 2

Percent ripe fruit by mid-June for Heintooga, Robeson and Premier blueberry cultivars. Castle Hayne, NC, 2005-2007

| | Percent ripe by mid-June | | | |
|---|---|---|---|---|
| Cultivar | 2005 | 2006 | 2007 | Mean |
| Heintooga | 40 | 92 | 85 | 72 |
| Robeson | 0 | 62 | 39 | 47 |
| Premier | 0 | 28 | 28 | 19 |
| Legacy[1] | | | 81 | |

[1]Southern highbush cultivar included for comparison in 2007.

Yield Per Plant

Yield per plant for 'Heintooga' was significantly lower than 'Robeson' or 'Premier' two years out of three at Castle Hayne, N.C., (Table 3). However, plant size of 'Heintooga' is smaller than either of the other two varieties (see Plant Dimensions under Botanical Description, and U.S. Plant Pat. No. 19,756), therefore 'Heintooga' does not have the same yield potential on a per plant basis as 'Robeson' or 'Premier'. Since 'Heintooga' is a smaller plant, the difference in yield on a per hectare basis can be compensated for by closer spacing of plants within rows.

TABLE 3

Yield in grams per plant for Heintooga, Robeson and Premier blueberry plants. Castle Hayne, NC. 2005-2007[1]

| | Yield (grams/plant)[2] | | |
|---|---|---|---|
| Cultivar | 2005 | 2006 | 2007 |
| Heintooga | 2532b | 1530b | 1384ns |
| Robeson | 5062a | 3531a | 2722ns |
| Premier | 5848a | 3096a | 1273ns |

[1]Mature plants, planted in a field that is a "frost pocket" (only field available at the time), so year to year variations in yield are due to frost and freeze injury.
[2]Values within columns not followed by the same letter are siginficantly different, P = 0.05, LSD test.

Fruit Size

'Heintooga' berries were statistically equal to those of 'Premier' in size two out of the three years (Table 4), which puts them in medium to large size categories. They were significantly larger than berries of 'Robeson' two out of the three years, and equal in size to 'Robeson' the third year.

TABLE 4

Berry size (grams/berry) for Heintooga, Robeson and Premier blueberry cultivars, Castle Hayne, NC. 2005-2007.

| | Berry size (g/berry)[1] | | |
|---|---|---|---|
| Cultivar | 2005 | 2006 | 2007 |
| Heintooga | 1.97a | 1,8b | 1.48ns |
| Robeson | 1.56b | 1.54c | 1.44ns |
| Premier | 1.74ab | 7a | 1.63ns |

[1]Values within columns not followed by the same letter are significantly different. P = 0.05, LSD test

Fruit Color

In addition to The Royal Horticultural Society Colour Chart, fruit color was also determined objectively by a Minolta Color Meter (Table 5). Objective fruit color measurements determined that 'Heintooga' was equal to 'Premier' for light blue fruit color two years out of three. It was significantly lighter blue than 'Robeson' two years out of three and there were no differences between the two the third year.

TABLE 5

Objective berry color measurements (L values) for Heintooga, Robeson and Premier blueberries. Castle Hayne, NC. 2005-2007.

| | Berry color (L values[1,2]) | | |
|---|---|---|---|
| Cultivar | 2005 | 2006 | Average |
| Heintooga | 19.3b | 22.3a | 20.8ns |
| Robeson | 17.9c | 19b | 1.84ns |
| Premier | 21.1a | 21.3a | 21.2ns |

[1]Determined by Minolta Color Meter where higher "L" values indicate lighter blue color.
[2]Values within columns not followed by the same letter are significantly different, P = 0.05. LSD test.

Fruit Firmness

Fruit firmness was determined objectively in grams/mm compression by a FirmTeck II Firmness Tester (Table 6). 'Heintooga' was significantly more firm than either 'Robeson' or 'Premier' in all three years of evaluations. In addition, 'Premier' was significantly more firm than 'Robeson' for all three years. A threshold value of 200 g/mm is often used as the minimum standard for superior firmness for blueberry fruit. Therefore, the fruit of 'Heintooga' ranged from moderately firm (176 g/mm in 2005) to firm (196 g/mm in 2007). This also means that the fruit of 'Heintooga' is sufficiently firm for shipment to distant markets, in contrast to 'Robeson'.

TABLE 6

Objective berry firmness (g/mm compression) for Heintooga, Robeson and Premier blueberries. Castle Hayne, NC. 2005-2007.

| | Berry firmness (grams/mm)[1,2] | | |
|---|---|---|---|
| Cultivar | 2005 | 2006 | 2007 |
| Heintooga | 176a | 189a | 196a |
| Robeson | 118c | 117c | 128c |
| Premier | 160b | 170b | 177b |

[1]Determined by FirmTeck II where 200 g/mm is the minimum standard for supetior firmness.
[2]Values within columns not followed by the same letter are signific ntly different, P = 0.05, LSD test.

Fruit Picking Scar

In addition to measuring the average diameter of the picking scar of the berries as part of the botanical description, picking scar was also evaluated subjectively for the technical description of 'Heintooga' (Table 7). This was based on a subjective rating scale of 10-90 where less than 60 is unacceptable, 60-69 is acceptable, 70-74 is good, 75-79 is very good and 80 and above is superior. 'Heintooga' and 'Premier' had picking scars in the very good range all three years, and they both were superior to 'Robeson' two out of three years.

TABLE 7

Picking scar subjective ratings for fruit of Heintooga, Robeson and Premier blueberries. Castle Hayne, NC. 2005-2007.

| | Picking scar ratings[1,2] | | |
|---|---|---|---|
| Cultivar | 2005 | 2006 | 2007 |
| Heintooga | 75.5ns | 75.6a | 78.4a |
| Robeson | 73.9ns | 73.2b | 77.2b |
| Premier | 75ns | 75.7a | 78.2a |

[1]Based on a subjective 10-90 rating scale where less than 60 is unacceptable, 60-69 is acceptable, 70-74 is good, 75-79 is very good, and 80 and above is supetior.
[2]Values within columns not followed, by the same letter are significantly different, P = 0.05, LSD test.

Fruit Flavor

There were no significant statistical differences among the three varieties with regard to subjective ratings for flavor. Overall ratings for all three were in the very good range as follows; 'Heintooga' (77), 'Robeson' (76) and 'Premier' (75). The flavor of 'Heintooga' can also be characterized as sweet and very aromatic, which is quite similar to its grandparent, *V. constablaeii* PI 346603.

Post Harvest Shelf-Life

'Legacy' southern highbush blueberry variety has proven to have good extended shelf-life (Cline, 2011), so it was compared to 'Heintooga', 'Robeson' and 'Premier' after seven days storage at 4.5° C. and 21° C. (Table 8). 'Heintooga' was equal to 'Legacy' after seven days storage at 4.5° C., but not at 21° C. Neither 'Robeson' nor 'Premier' were equal to 'Legacy' at either storage temperature.

TABLE 8

Post-harvest shelf-life of the fruit of Heintooga, Robeson and Premier, compared to Legacy southern highbush for percent sound fruit after seven days storage at 4.5° C. and 21° C., Castle Hayne, NC

| | Percent sound fruit[1] | |
|---|---|---|
| Cultivar | 4.5° C.[1] | 21° C. |
| Heintooga | 74 | 57 |
| Robeson | 30 | 19 |
| Premier | 60 | 56 |
| Legacy[2] | 78 | 72 |

[1]Based on four reps for each of four harvest dates.
[2]Legacy included for comparison as a successful cultivar for extended shelf-life and long distance shipping.

Propagation

'Heintooga' is easily propagated asexually by both hardwood and softwood stem cuttings. All plants have remained true to type across all generations of asexual propagation.

Chilling Requirement

Dormant buds on plants of 'Heintooga' require 800-1000 hours of temperatures below 4.5° C. to break dormancy in spring.

Plant Habit

'Heintooga' plants are semi-upright in plant habit (see FIG. 1 and H/W ratio of 1 under plant dimensions) while 'Robeson' has an upright plant habit (H/W ratio of 1.33).

Soil Adaptation

'Heintooga' is widely adapted to soils and has performed well on both light sandy soils as well as high organic soils.

Disease Reaction

'Heintooga' has not had a problem with either of the major fungal diseases affecting blueberries in North Carolina, stem canker (*Botryosphaeria corticis*) and stem blight (*Botryosphaeria dothidea*) up to this time, but it is not claimed to be resistant to either disease. It has been susceptible to blueberry red ringspot virus, so only virus tested nursery plants should be purchased. 'Heintooga' is also susceptible to *Phytophthora* root rot (*Phytophthora cinnamon*), so it is important to only establish plants on well drained sites.

DNA Fingerprinting-Background

During the past three decades several biochemical and DNA based assays have been developed to fingerprint human and plants. While biochemical assays such as isozymes were among the very first ones that were developed but they are limited in number and time consuming to generate. Genetic information is stored in cells as DNA, a long molecular chain, on which the linear order of four chemicals (called A, C, G, and T nucleotides) constitute individual genes. DNA based markers including restriction fragment length polymorphism (RFLP) (Saiki et al. 1985), random amplified polymorphic DNA (RAPD) (Williams et al. 1990), amplified fragment length polymorphism (AFLP) (Vos et al. 1995), simple sequence repeats (SSRs) (Tautz 1989), single nucleotide polymorphism (SNP) (Collins et al. 1997), single position polymorphism (SPP) (Stoffel et al. 2012), and targeted region amplification polymorphism (TRAP) (Palumbo et al. 2007). Genotyping with molecular markers is used for cultivar fingerprinting, detection of genetic diversity, assessment of population structure, mapping genes of interest, and for selection of desirable genotypes in breeding programs. The coding sequences of DNA that make up the genes are interrupted by long stretches of DNA that do not code for proteins and which are consequently called "non-coding DNA" or more loosely referred to as "junk DNA". In this "junk DNA", there are numerous chromosomal locations that contain short stretches of DNA where a particular sequence of 2-8 nucleotides is repeated in tandem a number of times.

Figure 3:
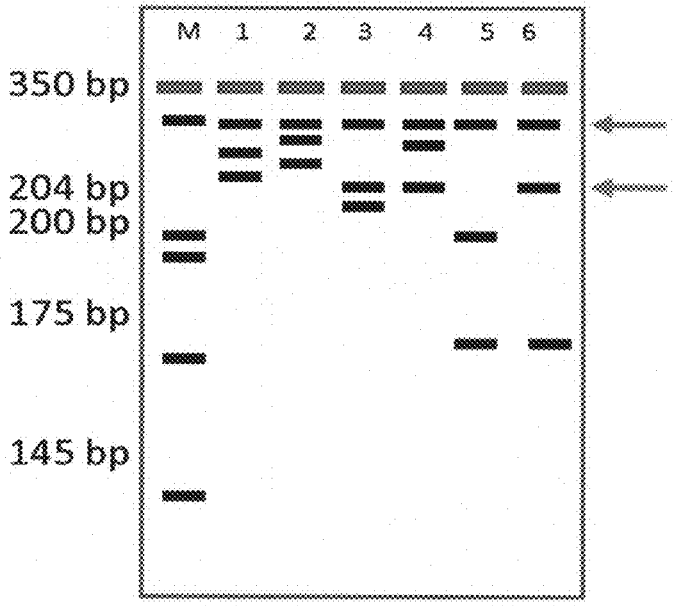
FIG. 3 relates to DNA fingerprinting of 'Heintooga'.
Figure 4:
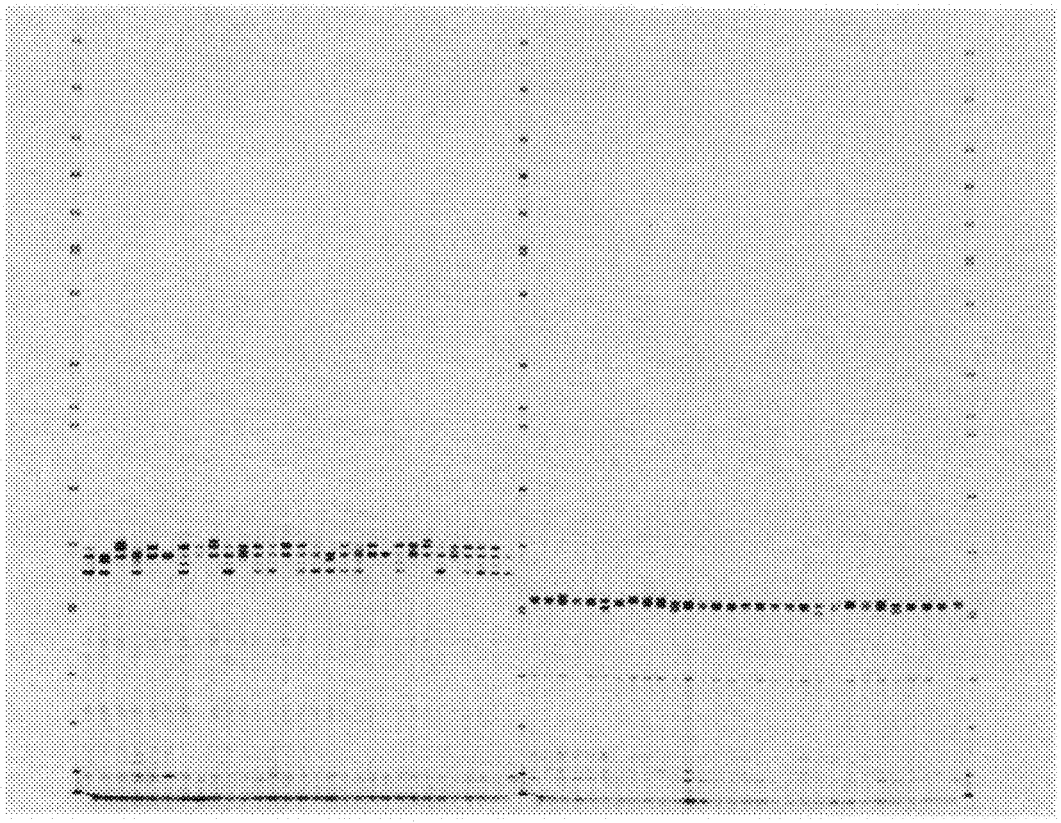
FIG. 4 provides a gel electrophoresis picture of two SSR markers run on 30 blueberry cultivars. The profile of the two SSR markers for different cultivars are different and shows that while the marker on the left hand side shows more polymorphism, the marker in the right hand side is less informative for distinguishing the cultivars.

These repeat units, known as SSRs, or microsatellites, always occur at the same chromosomal location, called "locus" and, although they are inherited stably from parent to child, they vary substantially between individuals. SSR markers are tandem repeats of di-, tri-, tetra- or pentanucleotides. For instance, common motif is ACn, where the two nucleotides A and C are repeated tandemly n times. The polymorphism occurs between two or more different cultivars when n differs among them. In another word, one cultivar can be $AC_{40}$ and another $AC_{50}$. The fragments can then be separated by size (bp=base pairs) on an electrophoresis gel and individuals can be genotyped for their allelic composition (homozygote or heterozygote for one or more alleles). Gel electrophoresis is a method for separation and analysis of macromolecules (DNA, RNA and proteins) and their fragments, based on their size and electrical charge (FIGS. 3 and 4). When these fragments amplified by polymerase chain reaction (PCR), one cultivar generates an 80 bp and other generates a 100 bp fragment, respectively. Usually amplification occurs in multiple locations in the genome (alleles), resulting multiple fragments with different sizes. A number of fragments will not be polymorphic between any two cultivars. Usually a few fragments will have different sizes that can be used to differential cultivars. Since each fingerprint is unique, therefore the profile of each cultivar must be checked against a pool of other cultivars that have been tested before.

A population database for blueberry has been developed at National Clonal Germplasm Repository in Corvallis (Oreg.), the most diverse global live genbank for blueberry and wild relatives, which includes over 1700 accessions from 39 countries and 81 blueberry species. They have genotyped these cultivars and accessions and created database of profiles for all genotypes that have been fingerprinted.

DNA Profiling of Heintooga

Plant Materials: Leaf tissues of Heintooga cultivar were collected from our experimental station field at Castle Hayne, N.C. as well as samples at Micropropagation and Repository Unit (MPRU) in Raleigh, N.C. This allowed us to compare the samples in the field with those that were used in tissue culture facility (MPRU) to make sure they are identical and the true types. The leaf tissues were kept in −80 freezer until they were used for DNA extraction.

DNA extraction: The DNA from frozen leaf tissue was extracted using QIAGEN DNeasy plant Mimi Kit (cat # 69104), according to manufacturer's recommendation. DNA quantity was measured using Qbit 3.0 Fluorometer (invitrogen, Carlsbad, Calif., USA) and Nanodrop (Desjardins and Conklin 2010) instruments.

PLR amplification: The polymerase chain reaction (PCR) was carried out on a Bio-Rad DNA Engine Dyad PTC0220 thermocycler. A multiplexed PCR primer master mix containing 2 μM of each primer was used to assay 5 markers in the same reaction (Table 9). The QIAGEN, Type-It® kit containing Taq DNA polymerase and other PCR components was used for amplification of DNA followed by manufacturer's recommendations.

The thermocycler was programmed according to QIAGEN recommendation. Briefly, an initial DNA denaturation and hot start step at 98° C. for 5 minutes, followed by 29 cycles of 95° C. for 30 sec, 57° C. for 1.5 min and 72° C. for 30 sec. A final extension was applied at the end of 29 cycles at 60° C. for 30 min and the samples were kept at 4° C. until further analyses were carried out.

TABLE 9

List of SSR markers, their names, size range, repeat motif, linkage group (LG) on a genetic linkage map, forward and reverse primers.

| SSR name | Size range | Motif | LG | Forward (5'-3') sequence | Reverse (5'-3') sequence |
|---|---|---|---|---|---|
| CA23 | 154-175 | (AGA)6 | 10 | GAGAGGGTTTCGAGGAGGAG | GTTTAGAAACGGGACTGTGAGACG |
| Contig179F | 19S-240 | (AGT)5 | 9 | CGTCGTGGAGGCTTAGAAAG | GTTTCAAAATCACCAGCACCAA |
| CfC262 | 237-287 | (CAC)8 | 2 | CGCCCACTCAGTTCATTCTT | ATAGGTGGTGGCTGGTGAGT |
| NA172F | 295-313 | (CAT)5 | 4 | CCTCGTCCTCCTCTTCCTCT | GTTTGACTTTGGAGAAGGCGAAG |
| Vac.288135 | 291-333 | (GAG)15 | 10 | TCTCTTTCCCTTTTCAAGTGG | GTTTATGATGGAATTCCGAGTTTG |

Detection: The size of each SSR marker was determined by Beckman Coulter CEQ 8000 Genetic Analysis System. This system automatically fills the capillary array with a patented linear polyacrylamide (LPA) gel, denatures and loads the sample, applies the voltage program, and analyzes the data. The fingerprint profile of Heintooga samples was developed based on five SSR markers. Each peak corresponded to one allele of markers used. The samples included a Heintooga sample collected from field F3 in Castle Hayne experimental station, a Heintooga sample collected from mother plant B grown on tissue cultured media, a Heintooga sample collected from mother plant C grown on tissue cultured media and a Heintooga sample collected from mother plant C grown in the greenhouse of MPRU, respectively.

Results: Heintooga generated a unique profile, which did not match with all cultivars that have been genotypes at National Clonal Germplasm Repository in Corvallis (Oreg.) (Table 10). The sample that was collected from our experimental station in Castle Hayne and the samples collected from MPRU (Tissue cultured plants in greenhouse and the plants that were still in the growth chamber in tissue culture media), all four generated identical profile indicating that they are true types in both locations and different sources. We cannot calculate the probability of finding an exact match with Heintooga in all blueberry populations, because allele frequency of all SSR alleles at all loci has not been calculated for blueberry. However, probability of all 19 alleles of the 5 markers tested is closed to zero.

TABLE 10

The fingerprint profile of the Heintooga based on five SSR markers. The numbers after the "-" designate the allele (different form) number of each marker and the numbers under each allele call is the size of the SSR markers in base pair

| Sample | CA23-1 | CA23-2 | Contig179-1 |
|---|---|---|---|
| Heintooga_F3_CH | 157 | 160 | 216 |
| Heintooga_B_TC_MPRU | 157 | 160 | 216 |
| Heintooga_C_TC_MPRU | 157 | 160 | 216 |
| Heintooga_C_GH_MPRU | 157 | 160 | 216 |

TABLE 10-continued

The fingerprint profile of the Heintooga based on five SSR markers. The numbers after the "-" designate the allele (different form) number of each marker and the numbers under each allele call is the size of the SSR markers in base pair

| Sample | Contig179-2 | Contig179-3 | Contig179-4 |
|---|---|---|---|
| Heintooga_F3_CH | 218 | 221 | 237 |
| Heintooga_B_TC_MPRU | 218 | 221 | 237 |
| Heintooga_C_TC_MPRU | 218 | 221 | 237 |
| Heintooga_C_GH_MPRU | 218 | 221 | 237 |

| Sample | Contig179-5 | CFC262-1 | CFC262-2 |
|---|---|---|---|
| Heintooga_F3_CH | 240 | 246 | 251 |
| Heintooga_B_TC_MPRU | 240 | 216 | 251 |
| Heintooga_C_TC_MPRU | 240 | 246 | 251 |
| Heintooga_C_GH_MPRU | 240 | 246 | 251 |

| Sample | CFC262-3 | CFC262-4 | NA172-1 |
|---|---|---|---|
| Heintooga_F3_CH | 254 | 260 | 295 |
| Heintooga_B_TC_MPRU | 254 | 260 | 295 |
| Heintooga_C_TC_MPRU | 254 | 260 | 295 |
| Heintooga_C_GH_MPRU | 254 | 260 | 295 |

| Sample | NA172-2 | NA172-3 | Vac.288135-1 |
|---|---|---|---|
| Heintooga_F3_CH | 304 | 307 | 310 |
| Heintooga_B_TC_MPRU | 304 | 307 | 310 |
| Heintooga_C_TC_MPRU | 304 | 307 | 310 |
| Heintooga_C_GH_MPRU | 304 | 307 | 310 |

| Sample | Vac.288135-2 | Vac.288135-3 | Vnc.288135-4 |
|---|---|---|---|
| Heintooga_F3_CH | 313 | 315 | 319 |
| Heintooga_B_TC_MPRU | 313 | 315 | 319 |
| Heintooga_C_TC_MPRU | 313 | 315 | 319 |
| Heintooga_C_GH_MPRU | 313 | 315 | 319 |

| Sample | Vac.288135-5 |
|---|---|
| Heintooga_F3_CH | 321 |
| Heintooga_B_TC_MPRU | 321 |
| Heintooga_C_TC_MPRU | 321 |
| Heintooga_C_GH_MPRU | 321 |

Herbarium Voucher

A voucher of 'Heintooga' will be deposited in the Herbarium of North Carolina State University (NCSU) in Raleigh, N.C., USA, upon patenting.

Literature Cited

Weakley, A. S. 2012. Flora of the Southern and Mid-Atlantic States. UNC Herbarium, North Carolina Botanical Garden, UNC-CH, Chapel Hill, N.C.

Ballington, J. R. and Rooks, S. D. 2009. Blueberry named 'Robeson'. U.S. Plant Pat. No. 19,756. US Patent and Copyright Office.

Sampson, B. J., Marshall-Shaw, D. A., Stringer, S. J., Sakhanokho, H. F., Werle, C. T. and Spiers, J. M. 2014. Improving yield and berry quality for zygomorphic bloom of blueberry; the role of plant growth regulators, gibberellic acid and coconut oil. Scientia Horticulturae. 173: 1-14.

United States Department of Agriculture, ARS. 1995. Release notice for 'Little Giant' blueberry.

United States Department of Agriculture. 2001. Notice of release of Legacy highbush blueberry. USDA and New Jersey Agr. Expt. Sta. 19 Dec. 2001. www.barc.usda.gov/psi/fl/ehl-leg.html Galletta, G. J. and Ballington, J. R. 1996. Blueberries, cranberries and lingonberries. Pp 1-107. In J. Janick and J. N. Moore (eds.) Fruit Breeding, Vol.II: Vine and Small Fruit Crops. John Wiley and Sons, Inc.

Cline, W. O. 2011. Blueberry cultivar 'Legacy'. The N.C. Blueberry Journal. Wednesday, Aug. 3, 2011.

Saiki R K, Scharf S, Faloona F, Mullis K B, Horn G T, Erlich H A, Amheim N: Enzymatic amplification of beta-globin genomic sequences and restriction site analysis for diagnosis of sickle cell anemia. *Science* 1985, 230(4732): 1350-1354.

Williams J G, Kubelik A R, Livak K J, Rafalski J A, Tingey S V: DNA polymorphisms amplified by arbitrary primers are useful as genetic markers. *Nucleic Acids Res* 1990, 18(22):6531-6535.

Vos P, Hogers R, Bleeker M, Reijans M, Lee Tvd, Homes M, Friters A, Pot J, Paleman J, Kuiper M et al: AFLP: a new technique for DNA fingerprinting. *Nucleic Acids Res* 1995, 23(21):4407-4414.

Tautz D: Hypervariability of simple sequences as a general source for polymorphic DNA markers. *Nucleic Acids Res* 1989, 17(16):6463-6471.

Collins F S, Guyer M S, Charkravarti A: Variations on a theme: cataloging human DNA sequence variation. *Science* 1997, 278(5343):1580-1581.

Stoffel K, van Leeuwen H, Kozik A, Caldwell D, Ashrafi H, Cui X, Tan X, Hill T, Reyes-Chin-Wo S, Truco M-J et al: Development and application of a 6.5 million feature affymetrix genechip® for massively parallel discovery of single position polymorphisms in lettuce (*Lactuca* spp.). *BMC Genomics* 2012, 13(1):185.

Palumbo R, Hong W-F, Wang G-L, Hu J, Craig R, Locke J, Krause C, Tay D: Target Region Amplification Polymorphism (TRAP) as a Tool for Detecting Genetic Variation in the Genus *Pelargonium*. *HortScience* 2007, 42(5):1118-1123.

Desjardins P, Conklin D: NanoDrop Microvolume Quantitation of Nucleic Acids. *Journal of Visualized Experiments: JoVE* 2010(45):2565.

SEQUENCE LISTING

<160> NUMBER OF SEQ ID NOS: 10

<210> SEQ ID NO 1
<211> LENGTH: 20
<212> TYPE: DNA
<213> ORGANISM: Vaccinium cultivar

<400> SEQUENCE: 1 gagagggttt cgaggaggag 20

<210> SEQ ID NO 2
<211> LENGTH: 20
<212> TYPE: DNA
<213> ORGANISM: Vaccinium cultivar

<400> SEQUENCE: 2 cgtcgtggag gcttagaaag 20

<210> SEQ ID NO 3
<211> LENGTH: 20
<212> TYPE: DNA
<213> ORGANISM: Vaccinium cultivar

<400> SEQUENCE: 3 cgcccactca gttcattctt 20

<210> SEQ ID NO 4
<211> LENGTH: 20
<212> TYPE: DNA
<213> ORGANISM: Vaccinium cultivar

<400> SEQUENCE: 4 cctcgtcctc ctcttcctct 20

<210> SEQ ID NO 5
<211> LENGTH: 21
<212> TYPE: DNA
<213> ORGANISM: Vaccinium cultivar

<400> SEQUENCE: 5 tctctttccc ttttcaagtg g 21

<210> SEQ ID NO 6
<211> LENGTH: 24
<212> TYPE: DNA
<213> ORGANISM: Vaccinium cultivar

<400> SEQUENCE: 6 gtttagaaac gggactgtga gacg 24

<210> SEQ ID NO 7
<211> LENGTH: 22
<212> TYPE: DNA
<213> ORGANISM: Vaccinium cultivar

<400> SEQUENCE: 7 gtttcaaaat caccagcacc aa 22

<210> SEQ ID NO 8
<211> LENGTH: 20
<212> TYPE: DNA
<213> ORGANISM: Vaccinium cultivar -continued

```
<400> SEQUENCE: 8

ataggtggtg gctggtgagt                                                20


<210> SEQ ID NO 9
<211> LENGTH: 23
<212> TYPE: DNA
<213> ORGANISM: Vaccinium cultivar

<400> SEQUENCE: 9

gtttgacttt ggagaaggcg aag                                            23


<210> SEQ ID NO 10
<211> LENGTH: 24
<212> TYPE: DNA
<213> ORGANISM: Vaccinium cultivar

<400> SEQUENCE: 10

gtttatgatg gaattccgag tttg                                           24
```

The invention claimed is:

1. A new and distinct variety of commercial blueberry plant (pentaploid trispecies *Vaccinium* hybrid) substantially as illustrated and described, characterized by its late mid-season to late season ripening, medium to large size fruit with good color, picking scar and flavor, moderately good to good firmness and good postharvest shelf-life making it suitable for long distance shipping, and averaging slightly less than one fully developed seed per berry so that the fruit should be perceived as seedless by most consumers.

* * * * *